(12) United States Patent
Lewis

(10) Patent No.: US 8,555,440 B2
(45) Date of Patent: Oct. 15, 2013

(54) PATIENT LIFTER WITH INTRA OPERATIVE CONTROLLED TEMPERATURE AIR DELIVERY SYSTEM

(76) Inventor: Randall J. Lewis, Bethesda, MD (US)

(*) Notice: Subject to any disclaimer, the term of this patent is extended or adjusted under 35 U.S.C. 154(b) by 123 days.

(21) Appl. No.: 12/150,730

(22) Filed: Apr. 30, 2008

(65) Prior Publication Data

US 2009/0271923 A1    Nov. 5, 2009

(51) Int. Cl.
*A47C 27/08* (2006.01)

(52) U.S. Cl.
USPC .............. 5/713; 5/81.1 HS; 5/423; 5/706; 5/710

(58) Field of Classification Search
USPC .......... 5/512, 423, 713, 613, 614, 652.2, 726, 5/710, 81.1 HS; 128/849
See application file for complete search history.

(56) References Cited

U.S. PATENT DOCUMENTS

| | | | | |
|---|---|---|---|---|
| 2,493,067 A * | 1/1950 | Goldsmith | | 5/726 |
| 3,644,950 A | 2/1972 | Lindsay et al. | | 5/709 |
| 3,667,073 A | 6/1972 | Renfroe | | 5/81.1 R |
| 3,740,777 A | 6/1973 | Dee | | 5/714 |
| 3,757,366 A | 9/1973 | Sacher | | 5/423 |
| 3,778,851 A | 12/1973 | Howorth | | 5/423 |
| 3,822,425 A | 7/1974 | Scales | | 5/710 |
| 4,279,044 A | 7/1981 | Douglas | | 5/714 |
| 4,391,009 A | 7/1983 | Schild et al. | | 5/713 |
| 5,022,110 A | 6/1991 | Stroh | | 5/710 |
| 5,109,560 A * | 5/1992 | Uetake | | 5/713 |
| 5,168,589 A | 12/1992 | Stroh et al. | | 5/710 |
| 5,249,318 A | 10/1993 | Loadsman | | 5/710 |
| 5,416,935 A * | 5/1995 | Nieh | | 5/423 |
| 5,483,709 A | 1/1996 | Foster et al. | | 5/81.1 R |
| 5,542,136 A * | 8/1996 | Tappel | | 5/710 |
| 5,561,873 A | 10/1996 | Weedling | | 5/713 |
| 5,590,428 A | 1/1997 | Roter | | 5/726 |
| 5,652,987 A | 8/1997 | Fujita | | 5/726 |
| 5,781,943 A | 7/1998 | Moenning et al. | | 5/81.1 C |
| 6,073,291 A * | 6/2000 | Davis | | 5/711 |

(Continued)

FOREIGN PATENT DOCUMENTS

| | | | |
|---|---|---|---|
| DE | 3320771 A1 | * | 12/1984 |
| GB | 2227943 A | * | 8/1990 |
| JP | 2002/000669 | | 1/2002 |
| WO | WO 8910110 A1 | * | 11/1989 |

*Primary Examiner* — Peter M Cuomo
*Assistant Examiner* — Brittany Wilson
(74) *Attorney, Agent, or Firm* — Ernest D. Buff; Ernest D. Buff and Assoc. LLC; Margaret A. LaCroix, Esq.

(57) ABSTRACT

An air mattress has a top chamber and a bottom chamber separated by a barrier. The patient rests on the top surface of the top chamber, which has a plurality of apertures discharging air through apertures that are not blocked by the patient. The top chamber is provided with temperature-controlled heated or cooled air at a regulated pressure. Heated or cooled air from the top chamber is delivered to an area substantially surrounding the patient. The bottom chamber has a bottom surface containing a plurality of apertures that remain closed due to the weight of the mattress and the patient when the pressure-regulated air is beneath a pre-selected value. When the air pressure is increased, the apertures at the bottom surface of the bottom chamber emit air, creating an air cushion underneath the air mattress that facilitates lateral movement of the mattress over a flat or irregular surface, such as from a hospital bed to a stretcher, or from a stretcher to an operating table.

9 Claims, 4 Drawing Sheets

(56) References Cited

U.S. PATENT DOCUMENTS

| | | | |
|---|---|---|---|
| 6,546,576 B1 | 4/2003 | Lin | 5/423 |
| 7,090,692 B1 | 8/2006 | Augustine et al. | 607/107 |
| 7,107,641 B2 * | 9/2006 | Davis | 5/710 |
| 7,114,204 B2 * | 10/2006 | Patrick | 5/81.1 R |
| 7,278,179 B2 * | 10/2007 | Schneider | 5/714 |
| 7,565,709 B2 * | 7/2009 | Davis | 5/710 |
| 7,627,910 B2 * | 12/2009 | Davis | 5/81.1 R |
| 7,735,164 B1 * | 6/2010 | Patrick | 5/81.1 HS |
| 7,914,611 B2 * | 3/2011 | Vrzalik et al. | 96/11 |
| 2001/0020303 A1 * | 9/2001 | Endo et al. | 5/421 |
| 2006/0010607 A1 * | 1/2006 | Schneider | 5/713 |
| 2007/0136952 A1 * | 6/2007 | Sargent | 5/726 |
| 2008/0000030 A1 * | 1/2008 | Wang | 5/713 |
| 2009/0056030 A1 * | 3/2009 | Bolden | 5/713 |
| 2009/0320211 A1 * | 12/2009 | Lau | 5/713 |

\* cited by examiner

PATIENT LIFTER WITH INTRA OPERATIVE CONTROLLED TEMPERATURE AIR DELIVERY SYSTEM

BACKGROUND OF THE INVENTION

1. Field of the Invention

The present invention relates to a patient transfer systems; and more particularly to a patient lifter mattress that supports a patient while at rest and provides heated or cooled air surrounding the patient during the resting period, or during intra operative transfers, increasing the level of comfort experienced by the patient.

2. Description of the Prior Art

The lateral transfer of patients, especially in the operating room, can be a difficult and poorly controlled procedure. Not only can the patient be injured during the process, but lateral patient transfer often contributes to back injuries incurred by hospital personal. The development of an air lifter, similar to a hovercraft, represents a significant advance in handling of patients. Making the device disposable has obvious advantages for sterility and cleanup. However, there is resistance in employing disposable lateral transfer devices for single usage because of associated costs. As a result, use of disposable lateral transfer devices is generally limited to special situations, such as when transporting very large patients. The patients may suffer from extreme cold or heat exposure during transport after a surgical procedure and controlling the temperature surrounding that patient with heated or cooled controlled temperature air delivery requires a tent having an enclosure, which is generally not portable.

In order to improve the usefulness of the lifter, combining the current transfer usage with that of an intra operative heater would make the device much more attractive for purchase by hospitals and surgical centers. Disposable intra operative heaters are already in general use, employing a simple heated air blower and a light plastic "tent". Thermal coverings have been provided. This device is broadly utilized throughout the world. Water blankets, the alternative, are mats filled with heated circulating water. While effective, these mats often come apart during patient transfer, causing a veritable flood on the operating room floor, and necessitating significant cleanup.

U.S. Pat. No. 3,644,950 to Lindsay et al. discloses a patient support system. Included with the system is a bed for supporting and treating a hospital patient. A lamination of low and medium density plastic foam is enclosed in a pressurized container. An open pore foam layer on top of the container produces a flow of air from the top of the foam layer for patient ventilation. Control of the volume of air varies the degree of ventilation. The pressurizing air for the container is controlled to vary the relative firmness of support. The patient support of the '950 patent provides ventilation around the patient delivered through foams of different density. The ventilation air is not heated. There is no discharge of air on the bottom surface of the patent support system enabling the creation of an air cushion that facilitates the lateral movement of a patient.

U.S. Pat. No. 3,667,073 Renfroe discloses a patient transporter. This apparatus provides for effortless moving of a non-ambulatory patient from a bed or operating table to a cart, e.g., recovery room stretcher or the like and from the cart to other non-porous surfaces, e.g., X-ray tables, etc. The patient transporter discharges compressed air through the apertures in the bottom of an inflatable mattress to levitate the mattress from an impervious stretcher or bed during lateral transport of the patient. The compressed air may be discharged from apertures provided on top of the inflatable mattress to essentially levitate the patient with burns or severe injury by a plurality of air jets. These air jets may aggravate the patient's injury. While the discharge of compressed air at the bottom of the inflatable mattress facilitates the lateral movement of the patient, the patient transporter does not provide heated air surrounding the patient.

U.S. Pat. No. 3,740,777 to Dee discloses a bed support. This bed support holds all or part of the human body and includes a chamber having an upper wall at least part of which is of thin flexible sheet material, e.g. rubber film, adapted when supported by gas pressure in the chamber to define a trough in which the item may lie. The body support device merely inflates balloons surrounding an individual body portion and the balloons have apertures that discharge air towards the body part through PTFE or polyethylene disks. This discharge of air through the apertures and the disk separates the balloons' external surfaces from the body part by the flow of air. No air is discharged on the bottom of the body support, with the result that a patient laying on the body support cannot be easily transported laterally. Moreover, no heated air is discharged to surround the patient and thereby provide warmth and comfort.

U.S. Pat. No. 3,757,366 to Sacher discloses a cushion for preventing and alleviating bedsores. The cushion for preventing and alleviating bedsores includes a warm air delivery system which delivers warm air in the close area of the cushion that contacts the skin of the patient, thereby preventing direct contact between the skin and the cushion and preventing or alleviating bedsores. No warm air is discharged below the cushion since the bottom portion of the cushion is indicated to be non-porous. Thus, the cushion with the patient laying there above may not be easily transported laterally.

U.S. Pat. No. 3,778,851 to Howorth discloses a mattress for use in treating a patient who has undergone extensive surgery or who has been severely burned. The mattress comprises an upper panel, a lower panel, and means for supplying air to the space between the two panels. The lower panel is made of air-impermeable material. At least a part of the upper panel is perforated to allow conditioned air to issue there from. The conditioned air impinges on and passes around the patient. It substantially isolates the patient from ambient air to reduce strain on the heart and promote healing. The mattress supplies conditioned air having proper temperature and humidity. Such air is free of bacterial contamination. It surrounds a patient that is supported on a mattress having a foam sponge support and air flow. The sponge supports the patient, while ribs allow air supply to pass through. The air surrounds the patient, preventing direct contact between the patient and the air permeable cover. Since the lower portion of the mattress is indicated to be impermeable, no air is delivered in the bottom of the mattress. As a result, a patient lying on the mattress may not be easily transported laterally.

U.S. Pat. No. 3,822,425 to Scales discloses an inflatable support appliance. The inflatable support apparatus of the '425 patent has an air impermeable base with air impermeable protrusions to which an air permeable cap is mounted. A person supported by these caps receives air through the apertures provided in the cap, preventing direct contact between the person and the cap. No air is delivered at the bottom, since the base and the protrusions are air impermeable. As a result, when a patient is supported by the caps, the lateral movement of the patient is very difficult, if not impractical.

U.S. Pat. No. 4,279,044 to Douglas discloses a fluid support system for a medical patient. Medical patients, such as those having burns or bed sores, are supported fully or in part by this fluid system. The system is directed to reducing local bearing pressure on body tissue. The fluid support system for a medical patient inflates a plurality of individual cell, which enlarge and contact the body and collapse as load of the patient is shared. No air is delivered between the patient and the walls of the cells. No air is released on the bottom of the support system and the lateral movement of the patient for example from a stretcher to an operating system is not easily possible.

U.S. Pat. No. 4,391,009 to Schild et al. discloses a ventilated body support. This ventilated support for living bodies comprises an inflatable alternating pressure pad, which is either enclosed by or forms a part of an air permeable plenum chamber through which air is pumped at low pressure to provide a source of ventilating air to a body resting on the support. The alternating pressure pad which is inflated by a high pressure pump has two sets of interdigitated cells which are alternately inflatable and deflatable and carry the weight of a body alternately, on each of the two sets of cells. The disclosed ventilated body support has a plurality support tubes comprising a high pressure central sealed portion and a low pressure surrounding portion each pressurized by two tubes with individual valves from a pump. The two portions may bleed air to the environment to adjust the support character of the ventilated body support. Heated air is not released surrounding the patient. No air is released in the bottom of the ventilated body support and a patient lying on the ventilated body support may not be laterally moved easily.

U.S. Pat. No. 5,022,110 to Stroh discloses a low air loss mattress. The low air loss mattress is made of multiple cushions, which are connected together and form an integral mattress which may be used on a standard hospital bed. The multiple cushions allow for variable pressure to support a patient and to compensate for different weights of various portions of the body of the patient. Each cushion is provided with air vents in its upper surface to provide air circulation around a patient and for pressure regulation in each cushion. The air may be heated. Retainers are provided to prevent billowing of each cushion in its center portions and maintain a substantially level patient support surface. A small portable blower provides a constant air supply for each of the cushions and allows adjustment of the air pressure in each of the cushions to accommodate varying weights of patients on the mattress. Any release of air occurs only on the patient contacting surface, and the air may be heated. There is no discharge of air on the bottom of the low air loss mattress. A patient lying on the mattress may not be easily moved laterally since there is no air cushion under the mattress assisting this movement.

U.S. Pat. No. 5,109,560 to Uetake discloses a ventilated air mattress with alternately inflatable air cells having communicating upper and lower air chambers. The ventilated air mattress with alternately inflatable air cells has a plurality of adjacent cells. One of the cells is inflated while the adjacent cell is deflated altering the support characteristic of the air mattress at a specific body contacting location so that no individual part of the body has to support the bodyweight over a period of time. The deflating of the cell is accomplished by opening a valve and the air is not heated and is not discharged surrounding the patient. No air is discharged from the bottom surface of the ventilated air mattress and therefore, moving a patient lying on the air mattress laterally is not assisted by an air cushion and therefore is very difficult.

U.S. Pat. No. 5,168,589 to Stroh et al. discloses a pressure reduction air mattress and overlay. This patent is a continuation in part of U.S. Pat. No. 5,022,110, discussed above. Multiple cushions allow for variable pressure to support a patient and to compensate for different weights of various portions of the body of the patient. Each cushion is provided with air vents in its upper surface to provide air circulation around a patient and for pressure regulation in each cushion. The air may be heated. Retainers are provided to prevent billowing of each cushion in its center portions and maintain a substantially level patient support surface. A small portable blower provides a constant air supply for each of the cushions and allows adjustment of the air pressure in each of the cushions to accommodate varying weights of patients on the mattress. Any release of air occurs only on the patient contacting surface and the air may be heated. There is no discharge of air on the bottom of the low air loss mattress and therefore a patient lying on the mattress may not be easily moved laterally since there is no air cushion under the mattress assisting this movement.

U.S. Pat. No. 5,249,318 to Loadsman discloses an air cushion support. This air inflatable support appliance has internally sealed seams, internal diaphragms and internal structural support members. The air cushion support of the '318 invention provides a flow of air between the top portion of the support and the patient lying there over requiring no cover or drawsheet. There is no discharge of air on the bottom of the air cushion support and the patient may not be transferred laterally from a stretcher to an operating table since no air cushion support is available at the bottom of the air cushion support. Moreover, presence of three or more individual cushions makes any movement of the patient lying on the bed very difficult.

U.S. Pat. No. 5,483,709 to Foster et al. discloses a low air loss mattress with rigid internal bladder and lower air pallet. This mattress has an upper patient supporting low air loss bladder for ventilating and preventing skin degeneration of a patient supported. An intermediate rigidly inflatable static bladder becomes relatively rigid upon inflation to aid in transferring or weighing a patient. A lower high air loss bladder is provided for reducing the friction force between the mattress and the supporting surface to facilitate surface-to-surface transfers. The high air loss bladder includes a peripheral tube, which seals against a supporting surface to contain the air, which escapes from longitudinal sacks within the tube. The foot sections of the low air loss and static bladders are selectively deflatable. The low air loss mattress has a low air loss bladder 12, an intermediate rigidly inflatable static bladder 14 and a lower high air loss bladder 18. The low air discharge bladder releases air surrounding the patient, reducing patient contact with the low air loss bladder. The air volume is generally small due to the small space separation between the patient and the top portion of the device. An intermediate pressurized rigid bladder supports the patient. The lower high air loss bladder serves to create an air cushion that allows the patient on the device to be moved easily. The low air loss bladder locally 'floats' the patient off the mattress surface. Moreover, the low air discharge air bladder does not provide heated air and does not have sufficient air delivery capacity to surround the area around the patient with warm air.

U.S. Pat. No. 5,561,873 to Weedling discloses an air chamber-type patient mover air pallet with multiple control features. This inflatable flexible pallet has rectangular dimensions defined by top and bottom sheets within which an array of structurally interrelated inflatable chambers are formed to support a load when inflated. The air chamber-type patient mover air pallet with multiple control features may be used for static support or a flow through system for moving a patient. Even though chambers are provided in the device, the chambers are generally interconnected and get the air from the air pressure source through valves. The compressed air may be at a high temperature due to pressurization of air and therefore may warm the ambient as well as the surface on which the patient is lying. The mattresses are generally made from polymeric material and this warming action may be too severe and uncontrolled and may damage the polymeric membrane of the mattress and injure the patient. The air chamber-type patient mover air pallet does not have two separate chambers disconnected from each other, the first chamber providing controlled heated or cooled air air surrounding the patient while a second separated chamber having adequate air flow to provide an air cushion for easy transverse movement of a patient.

U.S. Pat. No. 5,590,428 to Roter discloses an air pressurized person supporting device with ventilation. This device is particularly useful for comfortably supporting a person and includes a hollow member having upper and lower walls joined to each other around their periphery and adapted to be air pressurized. The upper wall is formed with a plurality of openings at spaced locations receiving a plurality of valve members, one for each opening. Each valve member is normally biased to a closed position with respect to its opening, but is engageable by a person supported by the hollow member and is moved thereby to an open position to outlet air from its respective opening. The air pressurized person supporting device with ventilation is pressurized by the application of air pressure. Valves in the supporting device seal off everywhere except where the person applies pressure, providing ventilation of air. The air is therefore released only under the patient and no air is released surrounding the person. Since no air is released under bottom surface of the support device, there is no air cushion. As a result, the patient cannot be transversely displaced easily. Further, the device does not provide heated air surrounding the patient.

U.S. Pat. No. 5,652,987 to Fujita discloses a decubitus ulcer prevention device. This decubitus ulcer prevention device comprises an air generator with a fan and an air mattress for receiving air from the air generator. Air is discharged at a surface through minute air discharge holes. A hose connects the air mattress to the air generator. Along a flow path of the air that passes through the fan are located, in order as named, a heater and an alkaline chlorine dioxide gas generator, in which is internally provided a ceramic body that is impregnated with an alkaline chlorine dioxide solution. Air that is heated, by passing through the heater, is brought into contact with the ceramic body, so that air that includes alkaline chlorine dioxide gas is thus supplied to the air mattress. The decubitus ulcer prevention device delivers heated air or ambient air treated with chlorine dioxide through fine apertures on the skin contacting surface of an air mattress. Air is not delivered on the underside of the air mattress and, as a result, the air mattress with the supported patient may not be easily displaced in a transverse direction.

U.S. Pat. No. 5,781,943 to Moenning et al. discloses a medical table and method for moving a patient from a first position to a second position. This medical table includes a base. The medical table with roller support uses a motor to rotate the rollers to change the position of the patient. No air is delivered on the bottom surface of the medical table. The lateral movement of the patient is not accomplished by the movement of an air mattress. Instead, the patient is driven by rollers and a belt under the patient, and has to be assisted by medical personnel for proper placement. Once the patient leaves this medical table, the patient has to be moved manually, causing hardship to the patient.

U.S. Pat. No. 6,546,576 to Lin discloses structure of a ventilated mattress with cooling and warming effect. This structure of a ventilated mattress with cooling and warming effect comprises a mattress body, a warming/cooling air-delivery controlling box, and a connecting tube. The control box produces warming/cooling air to the mattress body via the connecting tube and the warming/cooling air is released via a plurality of ventilation buttons mounted at the surface of the mattress body. Thereby, the mattress provides the user with a warming/cooling effect. The mattress is not an air mattress, but has conventional springs to support a patient positioned on the mattress. No air is delivered at the bottom surface of the mattress. Due to the absence of an air cushion at the bottom surface of the mattress, a patient lying on the mattress may not be laterally moved with ease.

U.S. Pat. No. 7,090,692 to Augustine et al. discloses a thermal blanket. This thermal blanket includes an inflatable covering with a head end, a foot end, two edges and an undersurface. The covering is inflated through an inlet at the foot end by a thermally-controlled inflating medium. An aperture array on the undersurface of the covering exhausts the thermally-controlled inflating medium from the covering. Exhaust port openings are provided at the edges of the covering to vent the inflating medium, which enhances circulation of the thermally-controlled medium through the cover. An uninflatable section is provided at the head end, together with an absorbent bib attached to the covering, adjacent the uninflatable section. When inflated, the thermal blanket self-erects and provides a bath of thermally-controlled inflating medium to the interior of the erected structure. The blanket has an aperture free top surface and a side facing the patient is provided with a plurality of apertures to discharge warm air that is supplied to the blanket. The portion of the blanket near the head of a patient is free from these apertures and functions as an apron. This is a thermal blanket that is provided with thermally controlled hot air and is not an air mattress that is provided with heated air. Further, there is no air discharge under the bottom surface of a mattress to facilitate lateral movement of a patient.

U.S. Pat. No. 7,114,204 to Patrick discloses a method and apparatus for transferring patients. This patient transfer apparatus includes an inflatable mattress, alternatively having a rigid top board with a patient restraint system on which a patient can be placed, when patient immobilization is required. A portable cart is included with a chamber for storage of a plurality of mattresses. The cart also has a gas/air blower and power supply system for empowering the blower. Pressurized air is supplied to a single chamber of an air mattress, which discharges the air through the underside of the mattress. While this passage of air creates an air cushion under the mattress, permitting lateral displacement of the patient, there is no indication that the pressure of supplied air is regulated. No warm air is delivered to the patient positioned on the upper surface of the mattress device.

Foreign Patent Publication No. JP2002000669 to Masato et al. discloses a bed and chair for nursing and care. The bed or chair is lifted upwards by pumping air into an air pad 11. No air is delivered at the bottom of a mattress to create an air cushion that facilitates movement of a patient. This '669 merely raises a bed or a chair.

"AirMatt-Patent Transfer System" at web location http://www.midmed.com.au/index.php?module=pagesetter&func=viewpub&tid=2&pid=55&header=1 discloses Airmatt|Lateral Air Transfer System. The AirMatt system only provides air at the bottom surface of the mattress for easy displacement of a patient. No heated air is delivered from the top surface of the mattress for providing comfort to the patient during intra operative transport.

"AirPal-Patient Air Lift" at web location http://www.airpal.com/manual1.pdf discloses a patient transfer system. The AirPal-Patient Air Lift has a mattress on which the patient is positioned. Air is supplied to the mattress to enable the lateral movement of the patient, who floats on an air cushion. The mattress is not moved. Rather, the floating patient is moved. No warm air surrounds the patient.

"Hover Tech International-HoverMatt" is found at web location http:/Hwww.hovermatt.com/. The brochure is available at http://www.hovermatt.com/media.pdf/HoverMatt Brochure.pdf. It discloses HoverMatt® Air Transfer Mattress. The HoverMatt provides air directly under the patient forming an air cushion so that the patient can be laterally slid on the mat. There is no air provided on the bottom surface of the mat forming an aircushion. The mat is not laterally slid. Instead, the patient is slid by an attendant. No warm air surrounds the patient.

There remains a need in the art for a mattress that supports a patient effectively at all times with minimal usage of compressed air while at the same time providing the functionality of a patient lifter for easy transfer of the patient from a stretcher to an operating table, bed or the like without straining the patient or hospital workers. There is also need for an air mattress that provides a supply of heated or cooled air surrounding the patient, increasing the patient comfort level without having to use tents and elaborate construction that limits the opportunity to observe the patient at rest or during intra operative transport.

SUMMARY OF THE INVENTION

The present invention provides a system and method for a patient lifter having intra operative delivery of controlled temperature air surrounding a patient. The system is generally a mattress having a bottom surface and a top surface, a heated air top compartment and an ambient air bottom chamber separated by a diaphragm. The top surface has a plurality of apertures therein. A heated air chamber has an inlet aperture attached to a hose. Heated air travels through the heated air chamber. Apertures on the top surface of the mattress deliver heated air to a patient positioned proximate to the top surface of the mattress. The patient lifter mattress ambient air bottom chamber is inflatable. It is constructed with small holes in the bottom surface to allow air to exit, creating an air cushion that slightly levitates the mattress above an impermeable surface of a stretcher or a bed. Such construction facilitates transfer of the patient from the stretcher to an operating table. When the pressure in the ambient air bottom chamber is small, the apertures on the bottom of the bed are blocked by the weight of the mattress. The latter discharges a minimal quantity of ambient air and serves to support the patient in a manner similar to a conventional air mattress. When the patient needs to be laterally displaced, the compressed air regulated pressure is increased to a higher level, allowing air to leak from the apertures provided in the bottom surface of the mattress. An air cushion is thereby created, substantially decreasing the friction for lateral displacement of the mattress, so that even a heavy patient may be moved with minimal effort. Advantageously, with this arrangement hospital personnel are spared the difficult work of moving the patient.

The patient lifter and intra operative controlled temperature air delivery generally comprises: a mattress having a bottom surface, a top surface, and a heating or cooling chamber top chamber, lifting bottom chamber, top and bottom chambers separated by a diaphragm. The top chamber is provided with apertures therein, wherein an inlet aperture is appointed for attachment to a hose. This hose is, in turn, adapted to supply heated or cooled air, which travels there through and communicates with apertures within the top surface of said mattress for delivering heated air or cooled air to surrounding portions of a patient lying proximate to said top surface of said mattress. The apertures directly below the patient are blocked by the patient, when the pressure in the top chamber is small with the result that heated air or cooled air is delivered strictly through the unblocked apertures, and surrounds the patient and the immediate surroundings. When the pressure in the top chamber is slightly increased, some portion of the patient's body blocks the apertures while other portions directly below the patient separate the top surface of the mattress from the body of the patient thereby preventing direct contact between the skin of the patient and the mattress. A patient generally moves in such a manner as to limit the contact pressure applied to a sore or other skin injury and the mattress gently provides heated or cooled area in these regions limiting contact between the sore or skin injury from the mattress as the patient selects a suitable posture. The pressure in the top chamber may be pulsed from a small value to a slightly larger value, periodically changing the distribution of patient contacting points with the top surface of the mattress to thereby relieve contact pressure at the sores for skin injury locations. Use of a surgical drape around the patient is sufficient to provide warmth to the patient without the need for a tent or other containment.

The present invention solves the problems associated with providing comfort to a patient wherein a single mattress provides heated or cooled air surrounding the patient, which is retained by a simple surgical drape placed on the patient similar to a blanket without need for a tent and other structures. The lower chamber of the mattress is supplied with pressure-regulated compressed air and apertures provided on the bottom surface of the lower chamber of the mattress are generally closed shut due to the weight of the patient and the mattress. However, when the patient needs to be laterally displaced, the compressed air regulated pressure is increased to a higher level allowing air to leak from the apertures provided in the bottom surface of the lower chamber of the mattress. An air cushion is created, causing the friction for lateral displacement of the mattress to be substantially decreased.

In an alternative embodiment of the invention, the ambient air delivery into the bottom compartment is divided into two sub compartments, one to the left side of the mattress and one to the right side of the mattress. Release of pressure on one side collapses the support on that side. The air mattress becomes tilted, enabling the patient to be easily moved onto an operating table, bed, or the like. With this embodiment, a heavy patient may be moved with minimal effort by hospital personnel. The pressure in the top two chambers may be maintained at a small value allowing full contact between the patient's skin and the top surface of the mattress or may be maintained at a slightly larger value permitting partial contact of the patient's body with the top surface of the mattress. In this embodiment also, the pressure in the two top chamber may be pulsed from a small value to a slightly larger value, periodically changing the distribution of patient contacting points with the top surface of the mattress so as to relieve contact pressure between the top surface of the mattress and sore or injured portions of the patient's body.

In a further embodiment of the invention, the lower chamber of the mattress is divided into two lateral compartments that extend along the length of the mattress. Each of the two individual compartments are pressured by regulated pressure which can be individually controlled. When the pressure in one of the compartments in the lower chamber of the mattress is reduced, the upper surface of the mattress tilts in the direction of the compartment with reduced pressure and the patient automatically moves downwardly onto an operating table, or is easily moved from an operating table to the mattress of the subject invention, positioned on a stretcher. Once the patient is firmly on the mattress of the subject invention, the pressure in the previously pressure released chamber may be brought to normal value and the patient is now positioned on the mattress in a horizontal plane.

In a further embodiment, the bottom chamber may be provided with an ambient air supply at a pressure that may be pulsed. The air pressure may be pulsed from a small value to a slightly larger value which is sufficiently low to prevent the mattress from floating. Thus the mattress becomes soft or rigid as the pressure is varied from a small value to a higher value. Preferably, the bottom section comprises a plurality of sections arranged in an interlocking "S" or comb-shaped configuration. Air pressure within these sections is alternately increased and decreased, creating along the top surface of the mattress a plurality of ridges when air pressure is greater in a first of the sections than the air pressure in a second of the sections. As air pressure in the first section decreases and air pressure in the second section increases, the ridges previously formed by the first section turn into valleys and the valleys formed by the second section become ridges. In this manner, the rigid mattress sections b-like contours on the top surface of the mattress especially when the top chamber is provided with a low pressure of heated or cooled air supply. Pressure independently applied to these alternating ribs in the lower section of the mattress cause the ribs to become alternatively harder and softer, thereby elevating them slightly in alternate fashion to change pressure applied to a patient lying on the mattress. Advantageously, the ridges or ribs alter the points of contact between the patient's skin and the top surface of the mattress thereby reliving pressure on sores or skin injury locations.

BRIEF DESCRIPTION OF DRAWINGS

The invention will be more fully understood and further advantages will become apparent when reference is had to the following detailed description of the preferred embodiments and the accompanying drawings, in which.

DESCRIPTION OF THE PREFERRED EMBODIMENTS

Patients are generally required to be transported from a hospital bed to an X-ray, CT or MRI facility for laboratory tests. A patient may also be required to be transported from the hospital bed to an operating table. Patients oftentimes labor under a poor health condition, so that any movement of the patient results in extreme discomfort to the patient. Further, patients with increased body weight are generally more difficult to move laterally and may cause injury to the patient as well as back injuries to hospital staff. Recent development of airlift mattresses, as for example those marketed by Air-Matt, AirPal or HoverMatt have resulted in an air mattress with air cushion-forming apertures thereunder, which enable a patient positioned on the mattress to be laterally displaced on a flat or irregular surface with minimal effort. The patient may be laterally moved from a hospital bed to a stretcher, or from a stretcher to an x-ray table or an operating table with ease. However, these airlift mattresses do not surround the patient with controlled temperature airflow. As a result the patient often experiences temperatures during the transport and transfer operations that are too cold or too warm. Conventional methods for ambient temperature control surrounding the patient require use of tents that, in turn, require the use of elaborate immobile hardware.

Figure 1A:
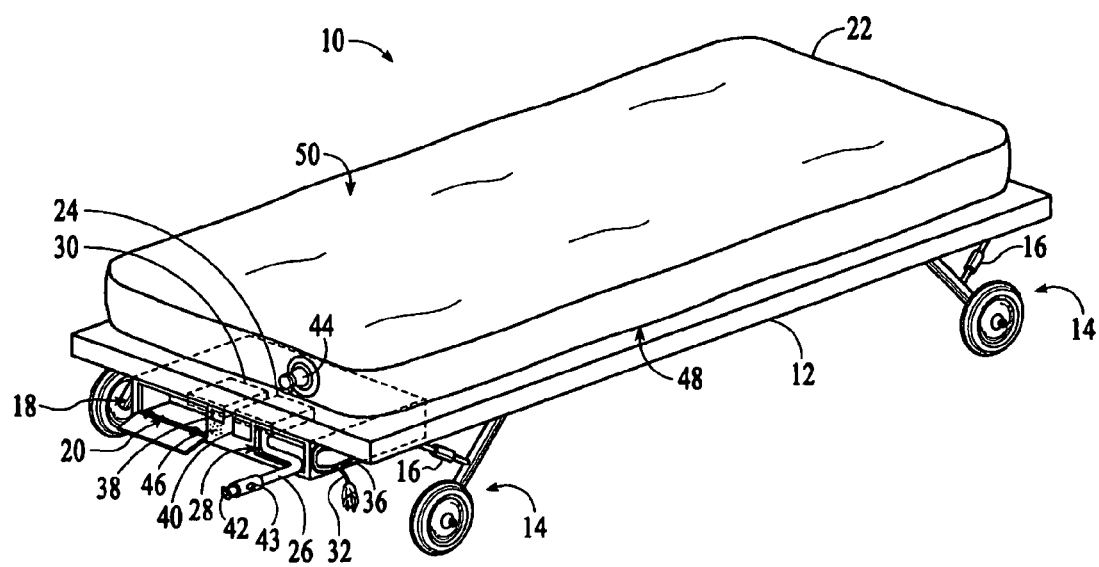
FIG. 1 illustrates an air mattress for patients of the type disclosed by the prior art.
Figure 1B:
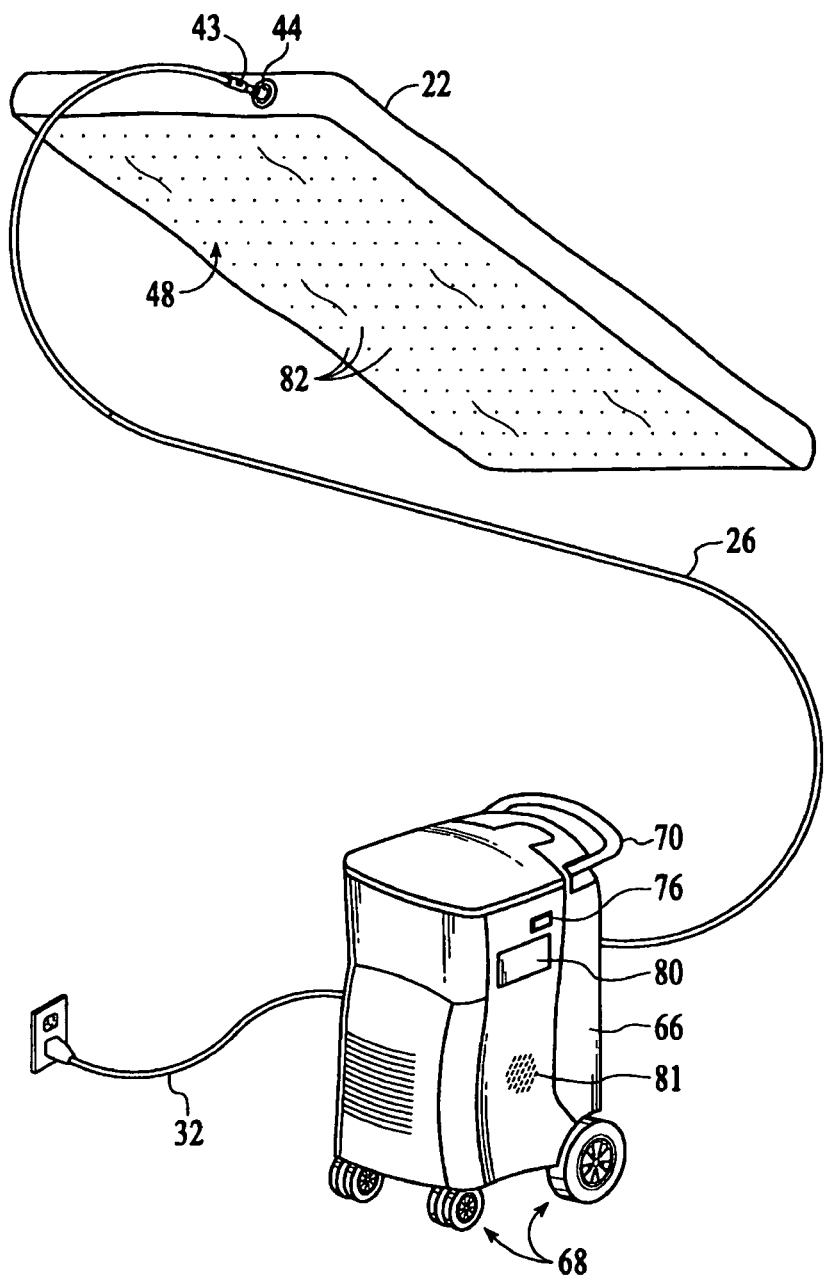
Figure 3:
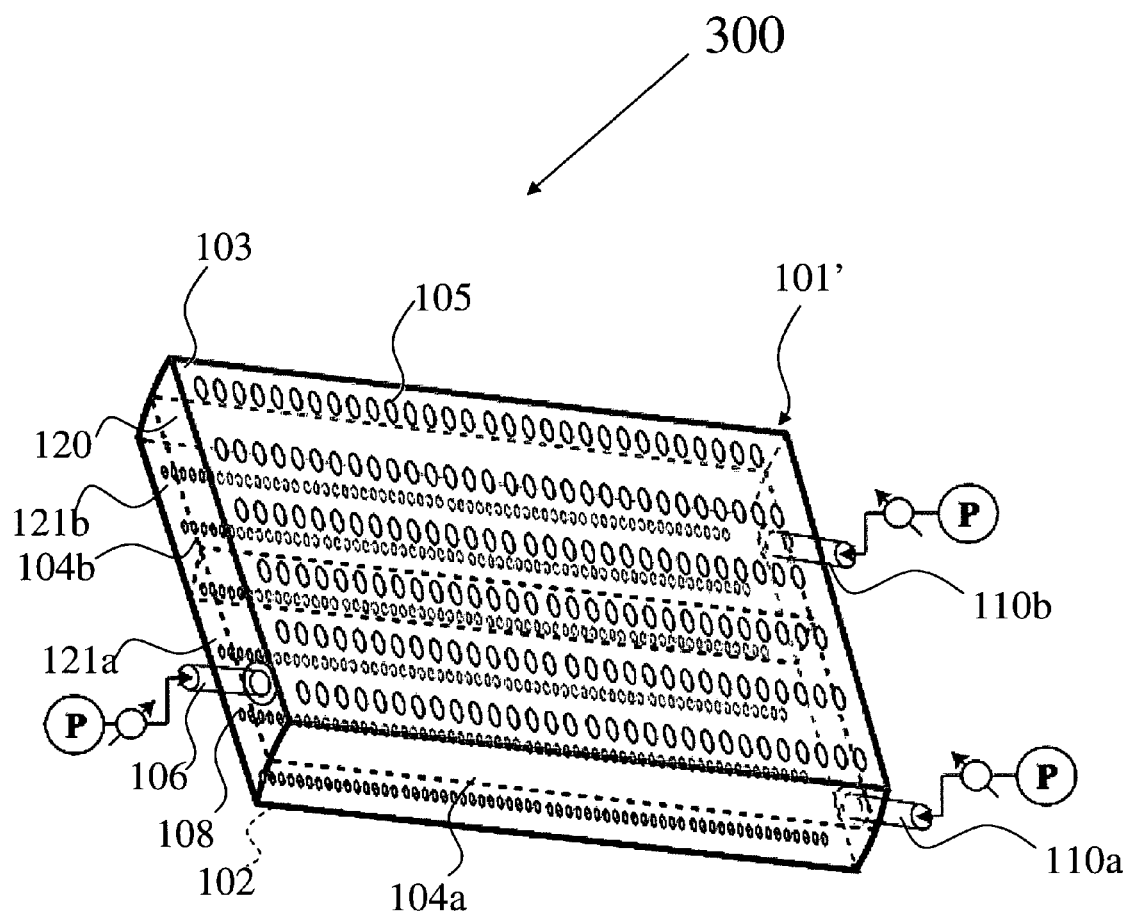
FIG. 3 illustrates a second embodiment of the subject invention.

FIGS. 1a and 1b depict a prior art inflatable air mattress disclosed by U.S. Pat. No. 7,114,204 to Patrick, which is laterally moved on an air jet cushion. This device is in contrast with the products marketed by AirMatt, AirPal or HoverMatt where the air jets are directly below the patient and the patient generally 'floats' on air, allowing easy displacement. FIG. 1a illustrates an integrated patient transfer system including an inflatable air mattress assembled on a stretcher 12 (FIG. 8 of the Patrick patent). The air cushion and supply cart according to Patrick is illustrated in FIG. 1b (FIG. 3 of the Patrick patent). The air mattress 22 is constructed with small holes in the bottom surface 48 to allow gas to exit from inside the mattress 22 so as to create an air cushion for levitating the air mattress. A substantial portion of the air mattress 22 (approximately 90%) is preferably constructed of nylon, making it less expensive to fabricate than other prior art air mattresses.

Figure 2:
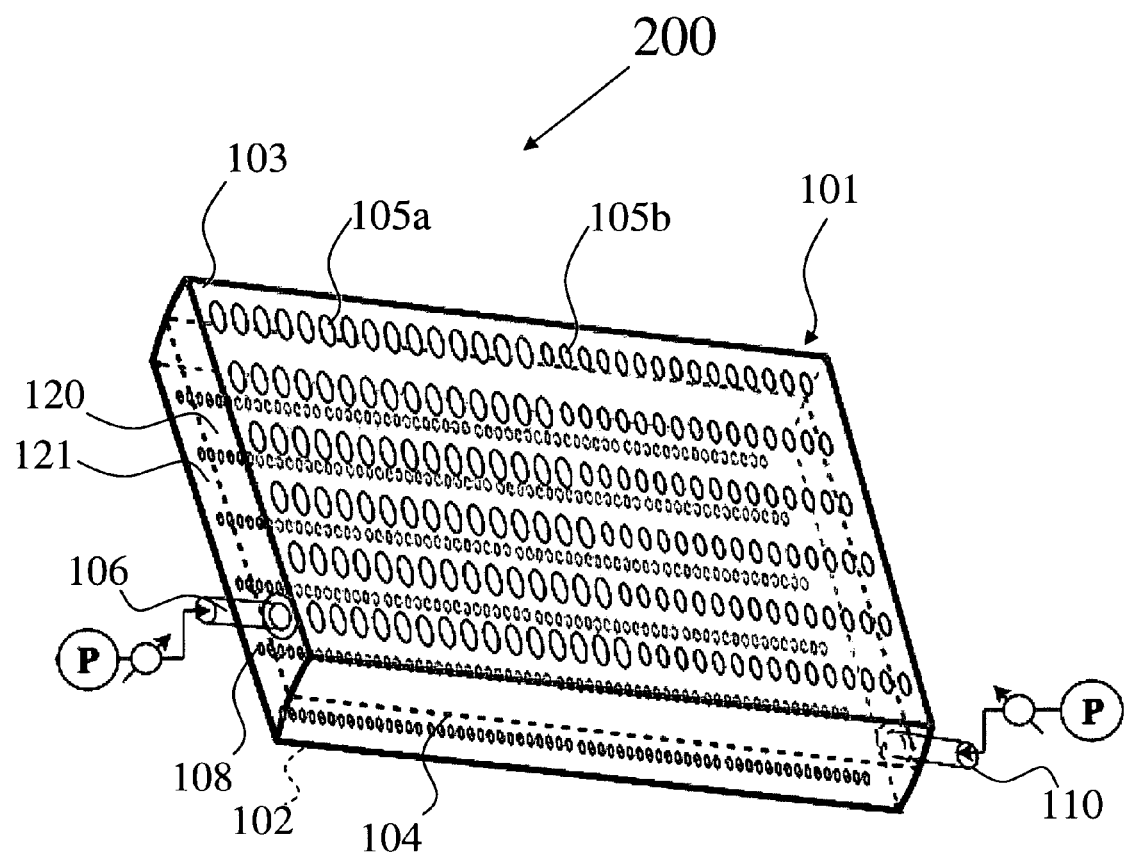
FIG. 2 illustrates a first embodiment of the subject invention.

FIG. 2 illustrates at 200 a first embodiment of the subject invention. Mattress 101 generally is provided with a top chamber 120 and a bottom chamber 121. Mattress 101 includes a bottom surface 102, a top surface 103, and a separation barrier 104 between the top chamber 120 and 121. Top surface 103 is appointed with apertures 105a and 105b therein. Generally, apertures 105a, located near the head portion of the mattress 101, are larger than apertures 105b located at the foot portion of mattress 101, delivering a higher quantity of comfort air to the upper portion of the body. The apertures 105a and 105b may be selected to be of equal size without departing from the scope of the invention. Low pressure compressed heated or cooled air supply to the top chamber 120 is provided through a hose attached to inlet 106. P indicates a pressure source and the circle with an arrow indicates a regulator. The heated or cooled air travels through the top chamber 120 and is delivered through the apertures 105a and 105b surrounding the patient lying on the mattress providing comfort, while the apertures of 105a and 105b directly below the patient are blocked. The mattress 101 functions as air lift mattress wherein the bottom chamber 121 is pressurized by ambient compressed air delivered at a pre-selected regulated pressure through the aperture 110. P indicates a pressure source and the circle with an arrow indicates a regulator. The bottom surface of the bottom chamber is provided with a plurality of apertures 108 through which the regulated pressure compressed air delivered through aperture may leak. When the regulated pressure of compressed air is delivered at a low regulated pressure, the weight of the patient and the mattress blocks the apertures and the bottom chamber is inflated, functioning in a manner similar to a conventional air mattress. However, when the pre-selected regulated compressed air pressure is increased to a high value, air leaks through the apertures 108 creating an air cushion between the bottom surface 102 of the mattress and underlying flat or uneven surface such as a bed, stretcher or an operating table. This air cushion essentially levitates the mattress with the patient slightly above the flat or uneven surface and the patient may be laterally displaced with minimal effort. Using this procedure, the patient is easily displaced laterally with minimal effort for example, from a bed to a stretcher or a stretcher to an operating table or any combination thereof. When the patient is moved to a desired location, the compressed air pressure may be brought to the pre-selected low pressure value and the mattress rests at the desired location without any movement, functioning as a conventional air mattress.

FIG. 3 illustrates at 300 the second embodiment of the subject invention. The intra operative controlled temperature device that can be used for heating and/cooling of the immediate area surrounding the patient, by providing the circulation of heated air or cooled air using a low pressure blower. Similar numerical indicia as FIG. 2 are used for clarity. Mattress 101' generally is provided with a top chamber 120 and a bottom chamber 121 separated from each other by a barrier 104a. In this second embodiment, the bottom chamber has two parallel longitudinal compartments 121a and 121b separated by a second barrier 104b. Compartments 121a and 121b are fed individually with their own regulated compressed air supply through inlets 110a and 110b as shown. P indicates a pressure source and the circle with an arrow indicates a regulator. Since inflation of each side of the air mattress is individually controlled, reducing pressure in one of the compartments essentially tilts the mattress along that direction allowing the patient to be gently rolled over, for example, into an operating table or a bed from a stretcher. Similarly, loading of a patient into a stretcher may also be facilitated by this tilting, since the patient could be rolled over onto the air mattress instead of having to be lifted and positioned thereon. Mattress 101 includes a bottom surface 102 with a plurality of apertures 108, which are blocked when the air mattress is on a flat or uneven surface and the regulated compressed air supplied at inlets 110a and 110b is low. In this condition, the mattress behaves in a manner similar to a conventional air mattress, with minimal air leakage at the bottom 102 of the mattress. However, when the regulated compressed air pressure supplied at inlets 110a and 110b is increased beyond a certain value, the air mattress levitates, creating an air cushion. With this feature, the mattress can be displaced laterally to move a patient thereon from a bed to a stretcher, or from a stretcher to an operating table or the like. If either regulated compressed air pressure supplied at inlets 110a or 110b is decreased, the side of the air mattress associated with that inlet dips down, allowing the patient to be rolled gently or otherwise easily transferred from the air mattress to an ordinary operating table, hospital bed or the like.

The key features of the patient lifter system wherein intra operative controlled temperature air surrounds a patient comprise, in combination:

i) a mattress with a top chamber and a bottom chamber separated by a barrier;

ii) said top chamber being provided with a plurality of small apertures on its top surface;

iii) said top chamber being provided with a low pressure supply of compressed heated air or cooled air;

iv) a patient lying on said top surface of the top chamber blocking the apertures immediately there below so that heated or cooled air delivered surrounds the patient when the pressure in the top chamber is set at a small value;

v) a patient lying on said top surface of the top chamber blocking the apertures immediately there below at a locus defined by contact interface between the patient's body and the top surface of the mattress, to thereby provide for patient/mattress contact involving regions that are free from sore or skin injury, while the heated or cooled air is delivered to surrounding areas where sore or skin injury may be present, and further preventing sore or skin injury resulting from contact between the injured portions of the patient's body and the top surface of the mattress when the pressure in the top chamber is set at a increased value;

vi) a surgical drape surrounding the patient to provide comfort to the patient without need for a tent or other hardware;

vii) said bottom chamber being provided with a supply of compressed ambient air at a pre-selectable regulated air pressure;

viii) said bottom chamber having a plurality of apertures on its bottom surface;

ix) said ambient air pressure inflating said bottom chamber and being portative to supporting a patient lying on the top surface of the top chamber in the manner of a conventional air mattress when apertures in the bottom surface are blocked by the weight of the mattress and the patient and the ambient pressure is of a pre-selected low value, minimally discharging ambient air; and x) during lateral movement of the patient lying on said mattress, the compressed ambient air pressure is increased to a pre-selected high pressure, discharging air through said bottom surface of said bottom chamber to thereby create an air cushion directly under the mattress with the patient allowing easy effort-free movement of the patient from a stretcher to an operating table or from a bed to a stretcher.

In a second embodiment, the mattress having a bottom chamber comprising two laterally separated compartments, each being provided with an individual regulated compressed ambient air supply, for collapsing one side to facilitate rolling of said patient onto an operating table or bed.

Advantageously, the Patient Lifter with Intra Operative Heater System provides:

i) a combination system with operative heater that delivers a warm or cold air stream surrounding a patient while apertures on the top surface are blocked by the patient, and a patient lifter/patient transport device;

ii) an intra operative heater device that delivers heat from beneath a patient and can be used without a tent, the system having surgical drapes that are placed above the patient and function as a cover when heat is delivered from beneath the patient;

iii) an air-cushion forming mechanism for developing compressed ambient air pressure that is increased to a pre-selected high pressure, discharging air through said bottom surface of said bottom chamber to thereby create an air cushion that facilitates lateral movement of the patient onto an operating table or a hospital bed; and iv) an intra operative device that can be used for heating and/cooling, by providing the circulation of hot or cool air through a low pressure blower.

Having thus described the invention in rather full detail, it will be understood that such detail need not be strictly adhered to, but that additional changes and modifications may suggest themselves to one skilled in the art. For example, mattress 101 can be provided with a plurality of channels, which are alternately inflated to a pressure controlled by a pressure regulator, thereby enabling adjustment to be made of the air pressure supplied to the channels in accordance with the weight and shape of the patient. The bottom section of the patient lifter can be divided into a plurality of interdigitating compartments that are pulsed from small pressure to a slightly larger pressure with a preselected pulse frequency, while the top chamber is maintained at a small pressure, causing the top surface of the mattress to replicate a rib-like contour created on the top surface of the bottom chamber upper surface. With this arrangement, the patient lifter functions as an alternating pressure mattress, redistributing points of contact pressure extant between the top surface of the mattress and body portions of a patient resting thereon to thereby avoid pressure sores and decubiti. The length and width of the mattress can be adjusted to produce a half-size mattress configuration that facilitates lateral movement of the upper torso or lower body portion of the patient. Such modifications are considered to fall within the scope of the invention as defined by the subjoined claims.

What is claimed is:

1. A patient lifter with intra operative controlled temperature air delivery system, comprising:
   a. an air inflated mattress having a top chamber and a bottom chamber separated by a diaphragm;
   b. said top chamber being a single chamber free from springs or barriers therein, said top chamber being supplied with a regulated controlled low pressure and controlled temperature heated or cooled air;
   c. said top surface of said top chamber having therein a plurality of air venting apertures capable of leaking heated or cooled air when said regulated controlled low pressure is supplied to said top chamber, thereby causing said heated or cooled air to surround a patient;
   d. said bottom chamber having a substantially flat bottom surface provided with a plurality of air venting apertures;
   e. said apertures located on said bottom surface of said bottom chamber being capable of leaking ambient air located within said bottom chamber when said bottom chamber is supplied with increased amounts of regulated controlled pressure air, thereby forming an air cushion beneath said bottom chamber that facilitates lateral displacement during patient transfer.

2. A patient lifter with intra operative controlled temperature air delivery system as recited by claim 1, wherein said air inflated bottom chamber is disposed on a hospital bed and a low bottom chamber pressure can also be maintained.

3. A patient lifter with intra operative controlled temperature air delivery system as recited by claim 2 utilizing a surgical drape appointed to contain a heated or cooled air stream in an area substantially surrounding the patient.

4. A patient lifter with intra operative controlled temperature air delivery system as recited by claim 1, wherein said lifter is disposed on a stretcher and low bottom chamber pressure can be maintained.

5. A patient lifter with intra operative controlled temperature air delivery system as recited by claim 4, wherein said air inflated mattress is disposed on a stretcher and, during lateral displacement of a patient on said air inflated mattress from said stretcher to an operating table, a high bottom chamber pressure is maintained, creating an air cushion under the bottom surface of the air inflated mattress that is appointed to facilitate lateral movement of the air inflated mattress and the patient.

6. A patient lifter with intra operative controlled temperature air delivery system as recited by claim 4, wherein said air inflated mattress is disposed on a stretcher and, during lateral displacement of said air inflated mattress from said stretcher to a hospital bed, a high bottom chamber pressure is maintained, creating an air cushion under the bottom surface of the air inflated mattress that facilitates lateral movement of the air inflated mattress and a patient lying on it.

7. A patient lifter with intra operative controlled temperature air delivery system as recited by claim 1, wherein said plurality of air venting apertures of said top surface of said top chamber comprises larger apertures located near a head portion and smaller apertures located at a foot portion of said top surface.

8. A patient lifter with intra operative controlled temperature air delivery system as recited by claim 1, wherein said air inflated device is disposable.

9. A patient lifter with intra operative controlled temperature air delivery system as recited by claim 1 comprising a single blower motor.

* * * * *